US012048702B2

(12) United States Patent
Ulmann et al.

(10) Patent No.: US 12,048,702 B2
(45) Date of Patent: Jul. 30, 2024

(54) FOLATE PREPARATIONS

(71) Applicant: APROFOL AG, Appenzell Steinegg (CH)

(72) Inventors: Martin Ulmann, Dachsen (CH); Gerd Wiesler, Dachsen (CH); Josef Flammer, Binningen (CH)

(73) Assignee: Aprofol AG (CH)

( * ) Notice: Subject to any disclaimer, the term of this patent is extended or adjusted under 35 U.S.C. 154(b) by 685 days.

(21) Appl. No.: 17/271,468

(22) PCT Filed: Aug. 29, 2019

(86) PCT No.: PCT/EP2019/073118
§ 371 (c)(1),
(2) Date: Feb. 25, 2021

(87) PCT Pub. No.: WO2020/043840
PCT Pub. Date: Mar. 5, 2020

(65) Prior Publication Data
US 2021/0308139 A1 Oct. 7, 2021

(30) Foreign Application Priority Data
Aug. 29, 2018 (EP) .................... 18191572

(51) Int. Cl.
*A61K 31/525* (2006.01)
*A61K 9/00* (2006.01)
*A61K 9/08* (2006.01)
*A61K 33/04* (2006.01)
*A61P 27/06* (2006.01)

(52) U.S. Cl.
CPC .......... *A61K 31/525* (2013.01); *A61K 9/0048* (2013.01); *A61K 9/08* (2013.01); *A61K 33/04* (2013.01); *A61P 27/06* (2018.01)

(58) Field of Classification Search
CPC .................................................. A61K 31/525
See application file for complete search history.

(56) References Cited

U.S. PATENT DOCUMENTS

| 6,103,756 | A | 8/2000 | Gorsek |
| 2004/0087479 | A1 | 5/2004 | Sosnowski et al. |
| 2008/0113900 | A1 | 5/2008 | Brasch et al. |
| 2011/0319356 | A1 | 12/2011 | Buell |
| 2015/0133455 | A1 | 5/2015 | Rekik |

FOREIGN PATENT DOCUMENTS

| JP | 2013544275 A | 12/2013 |
| WO | 2007076416 A2 | 7/2007 |
| WO | 2012073077 A1 | 6/2012 |
| WO | 2014177274 A1 | 11/2014 |

OTHER PUBLICATIONS

Giaconi, et al., "The Association of Consumption of Fruits/Vegetables with Decreased Risk of Glaucoma Among Older African-American Women in the Study of Osteoporotic Fractures", American Journal of Ophthalmology, Oct. 1, 2012, vol. 154, No. 4, pp. 635-644.
Scaglione et al., "Folate, Folic Acid and 5-methyltetrahydrofolate Are Not The Same Thing", Xenobiotica, 2014, vol. 44, No. 5, 9 pages.
Shipchandler et al., "Rapid, Fully Automated Measurement of Plasma Homocyst(e)ine with the Abbott IMx Analyzer", Clinical Chemistry, 1995, vol. 41, No. 7, pp. 991-994.
"Prevent Glaucoma With a Folate Supplement", Bottom Line Health, retrieved from the internet at https://bottomlineinc.com/health/glaucoma-prevent-glaucoma-with-a-folate-supplement, Jul. 24, 2014, 4 pages.
Brown, "Preservation of Retinal Structure and Function After Cilioretinal Artery Occlusion: A Case Report", International Medical Case Reports Journal, 2016, vol. 9, pp. 29-33.
Kang et al., "A Prospective Study of Folate, Vitamin B-6, and Vitamin B-12 Intake in Relation to Exfoliation Glaucoma or Suspected Exfoliation Glaucoma", JAMA Ophthalmology, 2014 vol. 132, No. 5, pp. 549-559.
Ramdas et al., "The Effect of Vitamins on Glaucoma: A Systematic Review and Meta-Analysis", Nutrients, 2018, vol. 10. No. 3, 14 pages.
Ramdas, "The Relation Between Dietary Intake and Glaucoma: A Systematic Review", ACTA Ophthalmologica: The Ophthalmological Journal of the Nordic Countries, 2018, vol. 96, No. 6, pp. 550-556.
Smolek et al., "Intervention with Vitamins in Patients With Nonproliferative Diabetic Retinopathy: A Pilot Study", Clinical Ophthalmology, 2013, vol. 7, pp. 1451-1458.
Wang et al., "Improving Diabetic and Hypertensive Retinopathy with a Medical Food Containing L-Methylfolate: A Preliminary Report", Eye and Vision, 2019, vol. 6, No. 21, 11 pages.
International Search Report and Written Opinion for International Application No. PCT/EP2019/073118, dated Dec. 9, 2019, 11 pages.

*Primary Examiner* — Golam M Shameem
(74) *Attorney, Agent, or Firm* — Buchanan Ingersoll & Rooney PC

(57) ABSTRACT

Preparations of folate for use in the treatment of eye disorders in the presence of elevated intraocular pressure. Methods of reducing intraocular pressure in a patient having an eye disease.

22 Claims, No Drawings

FOLATE PREPARATIONS

CROSS-REFERENCE TO RELATED APPLICATIONS

This application is a U.S. National Phase application of PCT International Application No. EP2019/073118, filed Aug. 29, 2019, which claims the benefit of European Application No. 18191572.9, filed Aug. 19, 2018, both of which are incorporated by reference herein in their entireties for all purposes.

FIELD OF THE INVENTION

The present invention relates to reduced folates and their use in the management of eye diseases.

BACKGROUND OF THE INVENTION

Diseases and degenerative conditions of the optic nerve and retina are the leading causes of blindness in the world. Worldwide there are approximately 300 million people suffering from different forms of visual impairment caused by these diseases. The most common diseases are optic neuropathies, retinopathies, and glaucoma.

There are numerous forms of optic neuropathy. One form is toxic neuropathy whereby the damage to the optic nerve is induced by a toxic compound such as methanol. Another form is nutritional neuropathy caused by nutritional deficiency of one or more micronutrients, such as folate and other B vitamins. Current methods for managing a nutritional deficiency are often based on oral supplementation. In the case of the eye however, this approach may not always be effective as the blood-retina barrier (BRB) in the retinal pigment epithelium could impede on the access of the nutrient into the site of the deficiency. BRB regulates, between the retinal blood vessels and the retina as well as between the choroid and the retina, similar to the blood brain barrier (BBB), the movement of solutes and nutrients from the choroid to the sub-retinal space.

Retinopathies are diseases leading to damage to the retina of the eyes often caused by abnormal blood flow. As in the case of optic nerve disorders there are various causes of retinopathies. Examples for retinopathies are diabetic (DR), hypertensive and genetic retinopathies. Age-related macular degeneration is technically a retinopathy but is often treated as a separate condition.

Glaucoma is a group of several distinct eye diseases that cause vision loss by damage to the optic nerve. Risk factors for glaucoma include increased intraocular pressure (IOP), genes, and high blood pressure. Glaucoma often develops as the eye ages, or it can occur as the result of an eye injury, inflammation, tumors, advanced cases of cataract or diabetes, or by treatment with steroids. Drug therapies that are used in glaucoma treatment reduce IOP either by decreasing vitreous humor production or by facilitating ocular draining. However, these medications suffer from poor patient compliance mainly due to side effects. Consequently, other treatments involving laser therapy and surgery have been developed but these are invasive and are temporary solutions.

US 2004/087479 discloses a composition comprising folic acid, vitamin $B_6$ and vitamin $B_{12}$ in combination with dextromorphan. This combination seems to lower homocysteine levels and inhibit the N-methyl-D-aspartate receptor which is considered to reduce the risk of glaucoma. Folic acid which is comprised in the composition, is the oxidized and biologically inactive form of folate. Reduced folates are not considered.

The publication "Prevent Glaucoma with a Folate Supplement", Bottom Line Health, 24 Jul. 2014, describes a folate deficit in people with pseudoexfoliation glaucoma (PEX) and elevated homocysteine levels. The intake of specific B-vitamins was considered as important to reduce the risk of PEX.

Kang Jae et al. (JAMA Ophthalmology, 30 Apr. 2014, volume 3, number 5, pages 549 to 559) describes a prospective study of folate, vitamin $B_6$, and vitamin $B_{12}$ intake in relation to exfoliation glaucoma or suspected exfoliation glaucoma. Homocysteine levels were taken as parameter and related to the intake of folate, mainly as folic acid, vitamin $B_6$ and $B_{12}$. Dietary intake data were retrieved from a pertinent database and patients had to complete a semi-quantitative food frequency questionnaire. Results suggested a trend for a lower risk for PEX and suspected PEX. The role of homocysteine was found to be inversely associated in patients with low folate intake having exfoliated glaucoma.

U.S. Pat. No. 6,103,756 discloses a composition comprising mainly anti-oxidative compounds such as vitamins A, C, E and herbal extracts as a supplement for patients with different eye diseases. The prevention of oxidative damage was indicated as primary goal. The composition contains high amounts of folic acid which results in unmetabolized folic acid in the body. Reduced folates were not considered.

Ramdas W. D. et al. (The effect of vitamins on glaucoma: a systematic review, Nutrients, 2018, 10, 359) published a meta-analysis on the association of vitamins with glaucoma. Subject to the study were patients with glaucoma. Only for the vitamins A and C a beneficial association between intake and open angle glaucoma was found. Vitamin B9 (folic acid) was also considered in the study. However, the synthetic and fully oxidized folate has different pharmacological properties and is not the active form in the body.

Giaconi J. A. et al (The association of Consumption of Fruits/Vegetables with decreased Risk of Glaucoma Among older African-American women in the Study of osteoporotic fractures, American Journal of Ophthalmology, volume 154, number 4, 1 Oct. 2012, pages 635 to 644) disclosed a study on the association between consumption of fruits/vegetables and the presence of glaucoma in older African-American women. The authors propose that a higher intake of vitamin A and C and carotenoids may be associated to a lower likelihood of glaucoma occurrence. Further, it was found that B vitamins (B1, B2, B3, B6), vitamin D and E and lycopene were not associated with a lower likelihood of glaucoma when taken in higher amounts. Other B vitamins (folate and B12) were not considered in this study.

Ramdas W. D. (The relation between dietary intake and glaucoma: a systematic review, Acta Ophthalmology, 2018, 96, 550-556) published a review with a meta-analysis on 46 studies investigating the effect of nutrients having anti-oxidative properties such as nitric oxide, carotenoids, flavonoids, glutathione, omega-6 and omega 3 fatty acids. Of these, only glutathione, nitric oxide and flavonoids show a protective effect on glaucoma. Selenium and iron seemed to have adverse effects by even increasing the risk of glaucoma. Flavonoids are derivatives of the base compound chromen-4-one. In addition, a prospective study like the Rotterdam study did not reveal a significant association between flavonoids intake and open-angle glaucoma. Thus, the evidence for an association of dietary intake of these compounds with glaucoma is still not strong. B vitamins were not investigated in this meta-analysis.

WO 2014/177 274 discloses stable aqueous solutions of reduced folates further comprising calcium. Alkaline salts of such reduced folates have a quite limited solubility so that there is a high risk of precipitate formation. No relation of eye diseases is mentioned.

WO 2007/076 416 discloses dietary supplements and methods for inhibiting the progression of macular degeneration and promoting a healthy vision. The dietary supplements contain vitamin E, carotenoids in the form of vitamin A, lutein and/or zeaxanthine. A vast number of additional ingredients are also contemplated, e.g. vitamin C, copper, zinc, rosemary, DHA and other vitamins and minerals. No information on or relation to glaucoma is provided.

Other treatment options include photodynamic therapy used either alone or in combination with photosensitive compounds and injections of inhibitors of the vascular endothelial growth factor (VEGF), as VEGF may cause growth of abnormal weak blood vessels under the retina. The secretion of VEGF is a reaction of the body to a prolonged insufficient supply of oxygen (hypoxia). Blocking the growth factor by chemical compounds or monoclonal antibodies blocks or reduces the formation of new blood vessels. VEGF is not only a cause for the breakdown of the blood-retinal barrier, VEGF generally plays a crucial role in angiogenesis. Its role concerns both physiologic and pathologic angiogenesis. VEGF synthesis is stimulated by ischemia through stabilization of hypoxia-inducible factor-1 (HIF). In addition, several cytokines such as IL-1a and IL-6 associated with intraocular inflammation also promote VEGF synthesis. Some of the most frequently occurring eye diseases, among them are age-related macular degeneration, diabetic retinopathy, retinal vein occlusion and retinopathy of prematurity (ROP), cause vision loss via VEGF-associated neo-vascularization of macular edema.

The currently available treatments are effective in slowing down the progression of eye diseases. They, however, do not cure the eye diseases. There is an ongoing need for effective treatments for ocular diseases such as macular degeneration (MD), age-related macular degeneration (AMD), diabetic retinopathy (DR), retinal and choroidal ischemia, glaucoma, cataracts, retinitis pigmentosa, choroidal neo-vascularization, retinal degeneration, ocular surface diseases and oxygen-induced retinopathy. Age-related vascular changes that occur systemically also affect ocular vascular beds. Studies show that ocular blood flow generally diminishes with age, which may result from an atherosclerotic process including an altered glycocalyx structure and narrowing of the retinal vessels. Endothelial dysfunction leads to decreased production of nitric oxide (NO), thereby increasing vascular tone and vasoconstriction, restricting blood flow and increasing intraocular pressure.

SUMMARY OF THE INVENTION

Micronutrients are compounds or substances, often referred to as vitamins and minerals, which although only required by the body in small amounts, are vital to development, disease prevention, and wellbeing. Micronutrients are not produced in the body and must be derived from the diet. For people, they include dietary trace elements in amounts generally less than 100 milligrams/day—as opposed to nutrients like omega-3 fatty acids which are required in larger quantities. The trace elements include at least iron, cobalt, chromium, copper, iodine, manganese, selenium, zinc and molybdenum. Micronutrients also include vitamins, which are organic compounds required as nutrients in tiny amounts by an organism. Deficiencies in micronutrients such as iron, iodine, vitamin A, vitamin $B_{12}$, vitamin D, folate and zinc can have devastating consequences.

Folic acid is a widely present growth factor having the character of a vitamin. Reduced folic acid is necessary for cells to divide properly as it is required for producing the genetic material DNA. As a result, cells and tissues that divide rapidly such as skin cells and intestinal cells are directly impacted by folic acid status.

In nature folates are present in the form of reduced folates carrying mono- or polyglutamate groups. Human metabolism is not capable of forming these folate compounds. Hence, folates have the character of a vitamin. De-novo synthesis of folate compounds only occurs in micro-organisms and plants. Folic acid itself is biologically inactive and must be enzymatically reduced via dihydrofolate reductase to 7,8-dihydrofolic acid and further to 5,6,7,8-tetrahydrofolic acid. Tetrahydrofolic acid (THF) is the biologically active form of folic acid. THF serves as carrier for $C_1$ units wherein the transfer is achieved via 5-Methyl-tetrahydrofolate, 5,10-Methylene-tetrahydrofolate, 5-Formyl-tetrahydro-folate, 5-Formimino-tetrahydrofolate, 10-Formyl-tetrahydrofolate and 5,10-Methenyl-tetrahydrofolat, respectively. $C_1$ units are for instance required in the synthesis of purine nucleotides and Desoxythymidin-5'-monophosphate. Folic acid is the oxidized form and the parent compound of biological folate. Because of its stability folic acid is used for supplements and food fortification. However, folic acid is not metabolically active and requires reduction and one carbon substitution before it is converted to 5-Methyl-(6S)-tetrahydrofolate by several enzymatically catalyzed steps. While the enzymatic conversion of folic acid itself may be incomplete, disrupted or reduced at several points of its pathway, the effect of its deficiency may be multiplied as the folate metabolism is linked to other metabolic cycles which means, that a malfunction in one cycle may induce malfunctions in other metabolic cycles. The blood retina (BRB) and blood-brain barrier (BBB) are critical for meeting the nutritional needs of the eye and the brain as certain nutrients are concentrated several-fold across the BRB and BBB. The BRB and BBB isolate the retina and the brain from the blood/vasculature and selectively transport small molecules to the retina and brain.

Numerous causes may promote or lead to a folate deficiency. For instance, an increased need for folate as seen during pregnancy and aging may eventually lead to a status of folate deficiency. Further, malabsorption of folate from food due to coeliac disease, intake of anti-metabolites such as methotrexate, aminopterin in cancer therapy used as competitive inhibitors of dihydrofolate reductase, and alcohol abuse may cause folate deficiency. Also, genetically founded malfunctions in one or more of the enzymes of folate metabolism may lead to folate levels below normal. In addition, inflammatory conditions may cause reduced folate levels which may be due to consumption of present folate and/or malabsorption of folate needed in repair processes of the tissue affected by the inflammation. In the skin, a lack of folate can lead to a condition called seborrheic dermatitis and may be related to vitiligo (loss of skin pigment). In diabetes, advanced glycation is one of the major pathways involved in the development and progression of different diabetic complications including nephropathy, retinopathy and neuropathy.

The consequences of a deficiencies in the folate status are numerous as are the roles folate plays in metabolism, e.g.

there occur disruptions in DNA methylation, in the amino acid, and nucleic acid metabolism. The latter being directly linked to the process of cell division. In tissue which shows a fast cell division such as bone marrow this may lead to megaloblastic anemia or thrombocytopenia.

There is thus an ongoing need for effective and safe preparations and methods for reducing intraocular blood pressure and improving retinal blood flow to better manage eye diseases.

DETAILED DESCRIPTION OF THE INVENTION

In a first aspect the invention provides a preparation for use in reducing intraocular pressure in a patient having an eye disease, the preparation comprising at least one folate in reduced form.

In a second aspect the invention provides a preparation for use in increasing total retinal blood flow in a patient having an eye disease, the preparation comprising at least one folate in reduced form.

The objects are achieved by a preparation including at least one folate in reduced form.

A preparation according to the present invention comprises a salt of at least one folate. The preparation is for use in the treatment of eye diseases in the presence of elevated intraocular pressure.

As normal intraocular pressure is considered a pressure between 10 mmHg and 20 mmHg. The average value of intraocular pressure is 15.5 mmHg with fluctuations of about 2.75 mmHg. A pressure above 20 mmHg is considered as elevated intraocular pressure. Lowering intraocular pressure below 20 mmHg might be beneficial and may delay progression of the disease.

In a further aspect, this invention provides a kit for use in reducing intraocular pressure in a patient having an eye disease, the kit comprising at least 10 daily doses of a preparation comprising at least one folate in reduced form. Preferably the pack comprises at least 60 daily doses of the preparation, for example about 90 daily doses.

In a yet further aspect, this invention provides a method of reducing intraocular pressure in a patient having an eye disease, the method comprising administering to the patient a preparation comprising at least one folate in reduced form. Preferably the patient is administered the preparation for at least 10 days, more preferably at least 60 days, most preferably 90 days.

In a yet further aspect, this invention provides a method of reducing the risk of raised intraocular pressure in a patient at risk of having an eye disease, the method comprising administering to the patient a preparation comprising at least one folate in reduced form. Preferably the patient is administered the preparation for at least 10 days, more preferably at least 60 days, most preferably at least 90 days.

In another embodiment the preparation is for use in the treatment of glaucoma. This disease condition is associated with the occurrence of elevated intraocular pressure. An example for a glaucoma is pseudoexfoliate glaucoma (PEX).

A further embodiment the preparation comprises in addition to the at least one folate salt one or more sulfur compounds. The sulfur compound is a compound comprising the sulfur atom. It may be an organic compound or a salt thereof.

In a preferred embodiment the preparation comprises one or more folate salts, one or more sulfur compounds and at least one vitamin.

The preparation for use in the treatment of eye diseases in the presence of elevated intraocular pressure may be a liquid or semi liquid formulation for a systemic application or a topical application to the eye.

Topical administration of a medication is understood as a medication that is applied to body surfaces such as the skin or mucous membranes. Many topical medications are epicutaneous, meaning that they are applied directly to the skin. Topical medications may also be applied to the eye as a route of administration, topical medications are contrasted with enteral (in the digestive tract) and intravascular/intravenous (injected into the circulatory system).

Preparations for systemic application may be liquid, semi-liquid or solid formulations.

In a preferred embodiment, the preparation further comprises at least one compound selected from the group consisting of vitamin B12, B6, B5, B2, B1, vitamin C, D, E, carotenoids, natural orange oil, and minerals. Minerals are for instance copper or zinc.

Natural orange oil is used as flavor compound masking other compounds such as sulfur compounds having disagreeable flavors. In addition, natural orange oil possesses antioxidant properties.

In another embodiment the preparation comprises the at least one folate salt and further at least one compound selected from the group consisting of selenium, cholecalciferol, pantothenic acid, vitamin B12, vitamin B6, vitamin B2, vitamin B1, zeaxanthine, lutein, vitamin E, vitamin C, copper salt, zinc salt, natural orange oil and a sulfur compound.

Optionally, the preparation may also comprise meso-zeaxanthine, omega-3 fatty acids or resveratrol. The latter belongs to the class of polyphenols and has antioxidative properties.

A suitable selenium compound is L-selenomethionine. The selenium compound may also be sodium selenite, sodium hydrogen selenite, or sodium selenate, Cholecalciferol is also known as vitamin D, in particular vitamin D3. Pantothenic acid may be present as dexpanthenol, calcium-D-pantotenate, or sodium-D-pantotenate. Vitamin B12 is comprised in the preparation in one of its different forms, such as methylcobalamin, cyanocobalamin, hydroxycobalamin, adenosylcobalamin. Vitamin B6 may be included as pyridoxine hydrochloride or pyridoxal-5'-phosphate. Vitamin B2 is for instance sodium-riboflavin-5'-phophate or riboflavin. Vitamin B1 may be thiamine hydrochloride or thiamine mononitrate. Vitamin E is included in one of its different forms, e.g. D-α-tocopherol, DL-α-tocopherol, D-α-tocopherol. Also, vitamin C may be present either as sodium-ascorbate, potassium-ascorbate, calcium-ascorbate, L-ascorbic acid, or L-ascorbyl-6-palmitate. The copper salt is either copper gluconate, copper citrate, copper oxide, or copper lysine complex. A suitable form of the zinc salt is zinc oxide, zinc gluconate, zinc lactate or zinc citrate. The natural orange oil is for instance natural orange extract, limonene, or myrcene. And the sulfur compound may be comprised as N-acetyl-cysteine, N-acetylcysteine amide, cysteine, lipoic acid, or methionine.

In another embodiment of the preparation according to the present invention the folate is selected from the group consisting of 5-methyl-(6S)-tetrahydrofolate, 5-formyl-(6S)-tetrahydrofolate, 5,10-methylene-(6R)-tetrahydrofolate, 5,10-methenyl-(6R)-tetrahydrofolate, 5-methyl-10-formyl-tetrahydrofolate, and 5-formyl-10-formyl-tetrahydrofolate and the cation of the folate salt is selected from the group consisting of calcium, sodium, zinc, arginine, choline, acetylcholine, N-methylaminoethanol, 2-amino-2-methyl-propanol, 1,1-dimethylbiguanidine, phenylethylbiguanidine, diaminoguanidine, glucosamine and dimethylaminoethanol.

In a further embodiment the preparation comprises the salt of at least one folate selected from the group consisting of 5-methyl-(6S)-tetrahydrofolate, and 5-formyl-(6S)-tetrahydrofolate, in the range of 0.15 mg to 1.8 mg, sulfur compound or a salt thereof in the range of 28 mg to 350 mg, selenium-compound in the range of 0.005 mg to 0.04 mg, cholecalciferol in the range of 0.009 mg to 0.06 mg. D-pantothenic acid in the range of 0.45 mg to 4 mg, vitamin B12 in the range of 0.003 mg to 0.98 mg, vitamin B6 in the range of 0.8 mg to 4 mg, riboflavin in the range of 2 mg to 14 mg, vitamin B1 in the range of 0.2 mg to 2 mg, zeaxanthine in the range of 1 mg to 3 mg, lutein in the range of 4 mg to 15 mg, vitamin E in the range of 1 mg to 8 mg, ascorbic acid in the range of 9 mg to 65 mg, natural orange oil in the range of 0.2 mg to 5.5 mg, copper in the range of 0.1 to 1 mg and zinc in the range of 7 mg to 33 mg.

In preferred embodiment the preparation comprises the salt of at least one folate selected from the group consisting of 5-methyl-(6S)-tetrahydrofolate, and 5-formyl-(6S)-tetrahydrofolate, in a range of 0.18 mg to 1.5 mg, sulfur compound or a salt thereof in the range of 29 mg to 316 mg, selenium in the range of 0.01 mg to 0.03 mg, cholecalciferol in the range of 0.015 mg to 0.045 mg, D-pantothenate in the range of 2 mg to 6 mg, vitamin B12 in the range of 0.005 mg to 0.6 mg, vitamin B6 in the range of 1.6 mg to 3.5 mg, riboflavin in the range of 3.7 mg to 10.5 mg, vitamin B1 in the range of 0.45 mg to 1.6 mg, zeaxanthine in the range of 1.9 mg to 2.1 mg, lutein in the range of 9 mg to 11 mg, vitamin E in the range of 2 mg to 6 mg, ascorbic acid in the range of 35 mg to 50 mg, natural orange oil in the range of 0.4 mg to 3.9 mg, copper in the range of 0.2 to 0.8 mg and zinc in the range of 11 mg to 26 mg.

In another preferred embodiment the preparation comprises the salt of at least one folate selected from the group consisting of 5-methyl-(6S)-tetrahydrofolate, and 5-formyl-(6S)-tetrahydrofolate, in the amount of 0.9 mg. N-acetylcysteine or a salt thereof in the amount of 180 mg, selenium as L-selenomethionine in the amount of 0.02 mg, cholecalciferol in the amount of 0.0375 mg, pantothenic acid as calcium-D-pantothenate in the amount of 5 mg, methylcobalamin in the amount of 0.5 mg, pyridoxal-5'-phosphate in the amount of 3 mg, riboflavin in the amount of 10 mg, thiamine mononitrate in the amount of 1.5 mg, zeaxanthine in the amount of 2 mg, lutein in the amount of 10 mg, D-α-tocopherol in the amount of 5 mg, calcium-ascorbate in the amount of 45 mg, natural orange oil, copper as copper-gluconate in the amount of 0.667 mg and zinc in the amount of 25 mg, the zinc in the form of zinc oxide.

A further embodiment of the preparation comprises the salt of at least one folate selected from the group consisting of 5-methyl-(6S)-tetrahydrofolate, and 5-formyl-(6S)-tetrahydrofolate, in the amount of 0.6 mg, N-acetylcysteine or a salt thereof in the amount of 100 mg, selenium as L-selenomethionine in the amount of 0.02 mg, cholecalciferol in the amount of 0.02 mg, pantothenic acid as calcium-D-pantothenate in the amount of 3 mg, methylcobalamin in the amount of 0.009 mg, pyridoxal-5'-phosphate in the amount of 2.1 mg, riboflavin in the amount of 4.2 mg, thiamine mononitrate in the amount of 0.55 mg, zeaxanthine in the amount of 2 mg, lutein in the amount of 10 mg. D-α-tocopherol in the amount of 3 mg, calcium-ascorbate in the amount of 40 mg, natural orange oil, copper as copper-gluconate in the amount of 0.3 mg and zinc as zinc oxide in the amount of 12.5 mg.

In a preferred embodiment the preparation comprises calcium-salt of L-5-methyl-tetrahydrofolate in an amount of 0.9 mg. N-acetylcysteine in an amount of 180 mg, selenium as L-selenomethionine in an amount of 0.02 mg, cholecalciferol in an amount of 0.0375 mg, pantothenic acid as calcium-D-pantothenate in an amount of 5 mg, methylcobalamin in an amount of 0.5 mg, pyridoxal-5'-phosphate in an amount of 3 mg, riboflavin in an amount of 10 mg, thiamine mononitrate in an amount of 1.5 mg, zeaxanthine in an amount of 2 mg, lutein in an amount of 10 mg, D-α-tocopherol in an amount of 5 mg, calcium-ascorbate in an amount of 45 mg, copper as copper-gluconate in an amount of 0.667 mg and zinc as zinc acetate in an amount of 25 mg.

In a preferred embodiment the preparation comprises calcium-salt of L-5-Methyl-tetrahydrofolate in an amount of 0.6 mg. N-acetylcysteine in an amount of 100 mg, selenium as L-selenomethionine in an amount of 0.02 mg, cholecalciferol in an amount of 0.02 mg, pantothenic acid as calcium-D-pantothenate in an amount of 3 mg, methylcobalamin in an amount of 0.009 mg, pyridoxal-5'-phosphate in an amount of 2.1 mg, riboflavin in an amount of 4.2 mg, thiamine mononitrate in an amount of 0.55 mg, zeaxanthine in an amount of 2 mg, lutein in an amount of 10 mg. D-α-tocopherol in an amount of 3 mg, calcium-ascorbate in an amount of 40 mg, copper as copper-gluconate in an amount of 0.3 mg and zinc as zinc acetate in an amount of 12.5 mg.

The preparation according to the present invention may be comprised in a tablet, a hard capsule or a soft gel capsule. These forms are suitable for systemic application.

Further suitable formulations are a solution, a patch, an ointment, a cream, a lotion, a nanoparticle formulation or a device for controlled and/or sustained release.

Besides elevated intraocular pressure, there is mounting evidence for the involvement of both vascular and immunological factors in the development of glaucomatous damage, with ischemia/reperfusion injury and inflammatory stress sharing a common outcome. Moreover, an association between glaucoma and various endocrine disorders has been described, and alterations of the autonomic nervous system were found. In addition, parallels with other neurodegenerative diseases, such as Alzheimer disease and Parkinson disease, have been observed.

Further evidence indicates that lowering intraocular pressure does not prevent progression in all patients; therefore, risk factors other than those related to intraocular pressure must be involved in the disease. The need for alternative, non-intraocular pressure-lowering treatments focused at preventing progression, such as neuroprotectants, are of interest to both the patient and the physician.

Three-month oral administration of antioxidants produced increases in biomarkers of ocular blood flow within retinal and retrobulbar vascular beds in patients with glaucoma (e.g. pseudoexfoliate glaucoma). Thus, the microcirculation of blood seems to play an important role regarding the glaucoma disease. Microvessel or microvasculature refers to the smallest systems of blood vessels in a body (e.g. arterioles, capillaries, venules), including those responsible for microcirculation, the system of smaller blood vessels that distribute blood and nutrients within organs and tissues. It may be measured in μl/min.

Microvascular processes may contribute to optic nerve head ischemia. Evidence for this includes changes to flow dynamics within the ophthalmic and retinal arteries of patients with glaucoma, an association between glaucoma and vascular disease, and acceleration of the glaucomatous process in the presence of nocturnal hypotension. Factors that lead to ocular arterial disease may indirectly contribute to the pathogenic process. Homocysteine is an independent risk factor for coronary artery disease, stroke, and venous thrombosis. More recently, elevated serum homocysteine has been shown to correlate strongly with vascular disorders that specifically affect the eye. These include retinal artery and retinal vein occlusion, non-arteritic anterior ischemic optic neuropathy, neovascular macular degeneration, and diabetic retinopathy. If open-angle glaucoma is in part an ocular vascular disorder, then homocysteine may also be associated with its development.

"Manage" means to address a medical condition or disease with the objective of improving or stabilising an outcome in a person or addressing an underlying nutritional need. Manage therefore includes treatment of the medical condition or disease, and the dietary or nutritional management of the medical condition or disease by addressing nutritional needs of the person. "Manage" and "management" have grammatically corresponding meanings.

For reducing intraocular eye pressure in an eye disease patient, the amount of the reduced folate in the preparation required to be administered will vary depending upon factors such as the risk and severity of the disease, any underlying medical condition or disease, age, the form of the preparation, and other medications being administered. Further the amount may vary depending upon whether the reduced folate is being used to reduce/increase (when the dose may be higher) or whether the reduced folate is being used during maintenance (when the dose may be lower). However, the required amount can be readily set by a medical practitioner and would generally be in the range from about 0.2 mg to about 50 mg per day, in certain embodiments from about 0.5 mg to about 15 mg per day, for example from about 0.8 mg to about 3 mg per day. An appropriate dose can be determined based on several factors, including, for example, body weight and/or condition, the severity of the disease being treated or prevented, other ailments and/or diseases, the incidence and/or severity of side effects and the manner of administration. Appropriate dose ranges may be determined by methods known to those skilled in the art. During an initial phase, the dosing can be higher (for example 0.2 mg to 100 mg per day, preferably 0.2 mg to 50 mg per day). During a maintenance phase, the dosing can be reduced (for example, 0.2 mg to 50 mg per day, preferably 0.5 mg to 15 mg per day, more preferably 0.6 mg to 3 mg).

For increasing total retinal blood flow in an eye disease patient, the amount of the reduced folate in the preparation required to be administered will vary depending upon factors such as the risk and severity of the disease, any underlying medical condition or disease, age, the form of the preparation, and other medications being administered. Further the amount may vary depending upon whether the reduced folate is being used to reduce/increase (when the dose may be higher) or whether the reduced folate is being used in during maintenance (when the dose may be lower). However, the required amount can be readily set by a medical practitioner and would generally be in the range from about 0.2 mg to about 50 mg per day, in certain embodiments from about 0.5 mg to about 15 mg per day, for example from about 0.8 mg to about 3 mg per day. An appropriate dose can be determined based on several factors, including, for example, body weight and/or condition, the severity of the disease being treated or prevented, other ailments and/or diseases, the incidence and/or severity of side effects and the manner of administration. Appropriate dose ranges may be determined by methods known to those skilled in the art. During an initial phase, the dosing can be higher (for example 0.2 mg to 100 mg per day, preferably 0.2 mg to 50 mg per day). During a maintenance phase, the dosing can be reduced (for example 0.2 mg to 50 mg per day, preferably 0.5 mg to 15 mg per day, more preferably 0.6 mg to 3 mg).

The administration of the preparation comprising the at least one folate in reduced form is preferably done over a period of 2 months to 12 months, more preferably over a period of 3 months to 8 months.

A method of reducing intraocular pressure in a patient having an eye disease, the method comprising administering the patient a preparation comprising at least one folate in reduced form.

At least one folate in reduced form for use in the management of intraocular pressure in a patient having an eye disease, comprising administering the patient the at least one folate in reduced form.

A preparation comprising least one folate in reduced form for management of intraocular pressure in a patient having an eye disease, comprising administering the patient the preparation comprising the at least one folate in reduced form.

A preparation comprising least one folate in reduced form for use in the management of intraocular pressure in a patient having an eye disease, comprising administering the patient the preparation comprising the at least one folate in reduced form.

A preparation comprising least one folate in reduced form for use in the treatment of intraocular pressure in a patient having an eye disease, comprising administering the patient the preparation comprising the at least one folate in reduced form.

EXAMPLE 1

A female patient suffering from pseudoexfoliate glaucoma (PEX) was examined on intraocular pressure on the occasion of two checks at the ophthalmologist. The first check was done on 5 Mar. 2019 and revealed an intraocular pressure of 15 mm Hg (right eye) and 15 mm Hg (left eye). From first of May 2019 until 21 Aug. 2019 the patient took one capsule of Ocufolin® forte the composition of which is indicated below. On the second check of the intraocular pressure, taking place on 13 Aug. 2019, the measurement of the intraocular pressure gave the following results, 12 mm Hg (right eye) and 12 mm Hg (left eye).

The decrease of the intraocular pressure from 15 mm Hg to 12 mm Hg in the period of approximately 3 months of daily intake of Ocufolin® forte is a significant decrease, even more taking into account that an intraocular pressure of 15 mm Hg is in the range of 12 mm Hg to 20 mm Hg which is considered as normal. Ocufolin® forte is a preparation comprising L-5-Methyl-Folate, respectively its calcium salt. The composition, respectively the amount of its active ingredients is as indicated below. The compounds forming the capsule are not indicated.

| Ocufolin ® forte | |
|---|---|
| Ingredient | Per Capsule |
| N-Acetylcysteine | 180 mg |
| Vitamin C (Ascorbic Acid) | 45 mg |

-continued

Ocufolin ® forte

| Ingredient | Per Capsule |
|---|---|
| Zinc (Zinc Oxide) | 25 mg |
| Vitamin B2 (Riboflavin) | 10 mg |
| Pantothenic acid (Ca-D-Pantothenate) | 5 mg |
| Vitamin E (natural Tocopherol) | 5 mg |
| Lutein | 10 mg |
| Vitamin B6 (Pyridoxal-5-Phosphate) | 3 mg |
| Vitamin B1 (Thiamine mononitrate) | 1.5 mg |
| Calcium-L-Methylfolate (Folate, 89) | 0.9 mg |
| Zeaxanthine | 2 mg |
| Copper (Copper Gluconat) | 0.667 mg |
| Vitamin B12 (Methylcobalamin) | 0.5 mg |
| Vitamin D3 (Cholecalciferol) | 37.5 mcg |
| Selenium (L-Selenmethionine) | 20 mcg |

EXAMPLE 2

The following tables show the results of seven exemplary patients taking part in a study to assess the effect of a 3-month L-methylfolate containing preparation over 12 weeks (1 capsule per day) on intraocular pressure, total ocular blood flow and systemic homocysteine plasma concentration in patients with diabetes. The preparation comprising the at least one folate in reduced form which was used in this study is Ocufolin® forte. The composition is as indicated in example 1. Except that 25 mg of zinc were comprised in the form zinc acetate.

Systolic, diastolic and mean blood pressures (SBP, DBP, MAP) were measured on the upper arm by an automated oscillometric device. Pulse rate was automatically recorded from a finger pulse-oxymetric device.

Intraocular pressure was measured with a slit-lamp mounted Goldmann applanation tonometer. Before each measurement one drop of oxybuprocainhydrochloride combined with sodium fluorescein was used for local anesthesia of the cornea.

Fourier domain optical coherence tomography (FDOCT) was used to determine total ocular blood flow. It is based on a local phase analysis of the backscattered signal and allows for bidirectional Doppler flow imaging. It does not need reference arm scanning and records one full depth and Doppler profile in parallel. The system operates with an equivalent A-scan rate of 25 KHz and allows real time imaging of the color encoded Doppler information together with the tissue morphology at a rate of 2-4 tomograms (40×512 pixel) per second. Despite the high detection speed a system sensitivity of 86 dB using a beam power of 500 μW at the cornea is achieved. The fundus camera allowed simultaneous view for selection of the region of interest. Bi-directional blood flow and pulsatility of blood velocity in retinal vessels with a Doppler detection bandwidth of 12.5 kHz and a longitudinal velocity sensitivity in tissue of 200 μm/s was observed. Diffuse luminance flicker was applied during the measurements for 60 seconds.

Plasma homocysteine levels determination was done by the CMIA (chemiluminescent one step microparticle immunoassay) method (Shipchandler, M. T. and E. G. Moore, Rapid, fully automated measurement of plasma homocyst(e)ine with the Abbott IMx analyzer. Clin Chem, 1995. 41(7): p. 991-4).

| Subject Nr. | Age | Gender (M/F) | Height (cm) | Weight (cm) | Medical history | Date of onset | Medical history | Date of onset | Ongoing | Medical history | Date of onset | Ongoing |
|---|---|---|---|---|---|---|---|---|---|---|---|---|
| 1 | 25 | F | 163 | 75 | Diabetes Mellitus Type I | NK/NK/00 | | | | | | |
| 4 | 51 | M | 186 | 67 | Diabetes Mellitus Type I | NK/NK/71 | Hypertension | NK/NK/11 | Yes | Hypercholesterolemia | NK/NK/11 | Yes |
| 9 | 38 | M | 188 | 108 | Diabetes Mellitus Type II | NK/NK/14 | Lasik o.u | NK/NK/09 | Yes | | | |
| 18 | 20 | F | 173 | 67 | Diabetes Mellitus Type I | 30 Apr. 2011 | | | | | | |
| 19 | 55 | F | 157 | 68 | Diabetes Mellitus Type II | NK/NK/89 | | | | | | |
| 23 | 56 | M | 183 | 85 | Diabetes Mellitus Type II | NK/NK/13 | Arterial Hypertension | NK/NK/02 | Yes | Calf Cramps | NK/NK/02 | Yes |
| 25 | 42 | M | 180 | 80 | Diabetes Mellitus Type II | NK/NK/11 | | | | | | |

NK: Not Known

Day 1 represents the start of the study while Day 2 represents the time point in the study after supplementation for 12 weeks.

| Subject Nr. | Blood pressure (mmHg) | |
|---|---|---|
| | Day 1 | Day 2 |
| 1 | 124/089 | 125/082 |
| 4 | 115/063 | 121/067 |
| 9 | 135/094 | 137/096 |
| 18 | 120/074 | 130/075 |
| 19 | 114/075 | 117/074 |
| 23 | 123/083 | 120/075 |
| 25 | 136/082 | 132/083 |

| Subject Nr. | Intraocular pressure of the right eye (mmHg) | | Intraocular pressure of the left eye (mmHg) | |
|---|---|---|---|---|
| | Day 1 | Day 2 | Day 1 | Day 2 |
| 1 | 13 | 12 | 13 | 11 |
| 4 | 17 | 13 | 17 | 12 |
| 9 | 15 | 11 | 16 | 11 |
| 18 | 17 | 11 | 14 | 12 |
| 19 | 15 | 10 | 13 | 12 |
| 23 | 16 | 12 | 17 | 12 |
| 25 | 18 | 14 | 15 | 14 |

Only five of seven subjects were tested on total ocular blood flow.

| Subject Nr. | Total Ocular Blood Flow (μl/min) | |
|---|---|---|
| | Day 1 | Day 2 |
| 1 | 37.7 | 38.4 |
| 4 | — | — |
| 9 | 17.7 | 21.9 |
| 18 | 55.0 | 61.7 |
| 19 | 39.6 | 45.5 |
| 23 | — | — |
| 25 | 33.2 | 38.9 |

| Subject Nr. | Homocysteine (μmol/L) | |
|---|---|---|
| | Day 1 | Day 2 |
| 1 | 10.1 | 5.3 |
| 4 | 16.9 | 7.5 |
| 9 | 14.6 | 10.3 |
| 18 | 8.7 | 5.1 |
| 19 | 13.4 | 9.6 |
| 23 | 17.6 | 12.5 |
| 25 | 11.3 | 6.2 |

The invention claimed is:

1. A preparation for use in reducing intraocular pressure in a patient having an eye disease, the preparation comprising at least one folate in reduced form, wherein the at least one folate in reduced form is selected from the group consisting of 5-methyl-(6S)-tetrahydrofolate, 5-formyl-(6S)-tetrahydrofolate, 5,10-methylene-(6R)-tetrahydrofolate, 5,10-methenyl-(6R)-tetrahydrofolate, 5-methyl-10-formyl-tetrahydrofolate, and 5-formyl-10-formyl-tetrahydrofolate and the folate salt is selected from calcium, sodium, zinc, arginine, choline, acetylcholine, N-methyl-aminoethanol, 2-amino-2-methyl-propanol, 1,1-dimethylbiquanidine, phenylethylbiquanidine, diaminoguanidine, glucosamine, and dimethylaminoethanol.

2. The preparation according to claim 1, wherein the preparation comprises a salt of the at least one folate in reduced form and at least one sulfur compound or a salt thereof.

3. The preparation according to claim 1, wherein the preparation comprises a salt of the at least one folate in reduced form and at least one antioxidant or a salt thereof or at least one vitamin.

4. The preparation according to claim 1, wherein the preparation is a liquid or semi liquid formulation configured for a topical application to an eye of the patient.

5. The preparation according to claim 1, wherein the preparation is a liquid, semi liquid or solid formulation configured for systemic application to the patient.

6. The preparation according to claim 1, wherein the preparation further comprises at least one compound selected from the group consisting of vitamin B12, B6, B5, B2, B1, vitamin C, D, E, carotenoids, natural orange oil, and minerals.

7. The preparation according to claim 6, wherein the preparation further comprises at least one compound selected from the group consisting of selenium, cholecalciferol, pantothenic acid, vitamin B12, vitamin B6, vitamin B2, vitamin B1, zeaxanthine, lutein, vitamin E, vitamin C, copper salt, zinc salt, natural orange oil, and a sulfur compound.

8. The preparation according to claim 1, wherein the preparation comprises a salt of the at least one folate in reduced form selected from the group consisting of 5-methyl-(6S)-tetrahydrofolate, 5-formyl-(6S)-tetrahydrofolate, in a range of 0.15 mg to 1.8 mg; and the preparation further comprises a sulfur compound or a salt thereof in a range of 28 mg to 350 mg; a selenium-compound in a range of 0.005 mg to 0.04 mg; cholecalciferol in a range of 0.009 mg to 0.06 mg; D-pantothenic acid in a range of 0.45 mg to 8 mg; vitamin B12 in a range of 0.003 mg to 0.98 mg; vitamin B6 in a range of 0.8 mg to 4 mg; riboflavin in a range of 2 mg to 14 mg; vitamin B1 in a range of 0.2 mg to 2 mg; zeaxanthine in a range of 1 mg to 3 mg; lutein in a range of 4 mg to 15 mg; vitamin E in a range of 1 mg to 8 mg; vitamin C in a range of 9 mg to 100 mg; natural orange oil in a range of 0.2 mg to 5.5 mg; copper in a range of 0.1 to 1 mg; and zinc in a range of 7 mg to 33 mg.

9. The preparation according to claim 1, wherein the preparation comprises a salt of the at least one folate in reduced form selected from the group consisting of 5-methyl-(6S)-tetrahydrofolate, 5-formyl-(6S)-tetrahydrofolate, in a range of 0.18 mg to 1.5 mg; sulfur compound or a salt thereof in a range of 29 mg to 316 mg; selenium in a range of 0.01 mg to 0.03 mg; cholecalciferol in a range of 0.015 mg to 0.045 mg; D-pantothenic acid in a range of 2 mg to 6 mg; vitamin B12 in a range of 0.005 mg to 0.6 mg; vitamin B6 in a range of 1.6 mg to 3.5 mg; riboflavin in a range of 3.7 mg to 10.5 mga vitamin B1 in a range of 0.45 mg to 1.6 mga zeaxanthine in a range of 1.9 mg to 2.1 mg; lutein in a range of 9 mg to 11 mg; vitamin E in a range of 2 mg to 6 mg; vitamin C in a range of 35 mg to 50 mg; natural orange oil in a range of 0.4 mg to 3.9 mg; copper in a range of 0.2 to 0.8 mg; and zinc in a range of 11 mg to 26 mg.

10. The preparation according to claim 1, wherein the preparation comprises a salt of the at least one folate in reduced form selected from the group consisting of 5-methyl-(6S)-tetrahydrofolate, 5-formyl-(6S)-tetrahydrofolate, in an amount of 0.9 mg; N-acetylcysteine or a salt thereof in an amount of 180 mg; selenium as L-selenomethionine in an amount of 0.02 mg; cholecalciferol in an amount of 0.0375 mg; pantothenic acid as calcium-D-pantothenate in an amount of 5 mg; methylcobalamin in an amount of 0.5 mg; pyridoxal-5'-phosphate in an amount of 3 mg; riboflavin in an amount of 10 mg; thiamine mononitrate in an amount of 1.5 mg; zeaxanthine in an amount of 2 mg; lutein in an amount of 10 mg; D-α-tocopherol in an amount of 5 mg; calcium-ascorbate in an amount of 45 mg; natural orange oil; copper as copper-gluconate in an amount of 0.667 mg; and zinc as zinc oxide in an amount of 25 mg.

11. The preparation according to claim 1, wherein the preparation comprises a salt of the at least one folate in reduced form selected from the group consisting of 5-methyl-(6S)-tetrahydrofolate and 5-formyl-(6S)-tetrahydrofolate, in an amount of 0.6 mg; N-acetylcysteine or a salt thereof in an amount of 100 mg; selenium as L-selenomethionine in an amount of 0.02 mg; cholecalciferol in an amount of 0.02 mg; pantothenic acid as calcium-D-pantothenate in an amount of 3 mg; cyanocobalamin in an amount of 0.009 mg; pyridoxal-5'-phosphate in an amount of 2.1 mg; riboflavin in an amount of 4.2 mg; thiamine mononitrate in an amount of 0.55 mg; zeaxanthine in an amount of 2 mg; lutein in an amount of 10 mg; D-α-tocopherol in an amount of 3 mg; calcium-ascorbate in an amount of 40 mg; natural orange oil; copper as copper-gluconate in an amount of 0.3 mg; and zinc as zinc oxide in an amount of 12.5 mg.

12. The preparation according to claim 1, wherein the preparation is in a form of a tablet, a hard gel capsule, or a soft gel capsule.

13. The preparation according to claim 1, wherein the preparation is in a form of a solution, a patch, an ointment, a cream, a lotion or an application for a controlled or sustained release.

14. A kit for use in reducing intraocular pressure, in a patient having an eye disease, the kit comprising at least 10 daily doses of a preparation comprising at least one folate in reduced form, wherein the at least one folate in reduced form is selected from the group consisting of 5-methyl-(6S)-tetrahydrofolate, 5-formyl-(6S)-tetrahydrofolate, 5,10-methylene-(6R)-tetrahydrofolate, 5,10-methenyl-(6R)-tetrahydrofolate, 5-methyl-10-formyl-tetrahydrofolate, and 5-formyl-10-formyl-tetrahydrofolate and the folate salt is selected from calcium, sodium, zinc, arginine, choline, acetylcholine, N-methylaminoethanol, 2-amino-2-methyl-propanol, 1,1-dimethylbiquanidine, phenylethylbiquanidine, diaminoquanidine, glucosamine, and dimethylaminoethanol.

15. A method of reducing intraocular pressure in a patient having an eye disease, the method comprising administering to the patient a preparation comprising at least one folate in reduced form, wherein the at least one folate in reduced form is selected from the group consisting of 5-methyl-(6S)-tetrahydrofolate, 5-formyl-(6S)-tetrahydrofolate, 5,10-methylene-(6R)-tetrahydrofolate, 5,10-methenyl-(6R)-tetrahydrofolate, 5-methyl-10-formyl-tetrahydrofolate, and 5-formyl-10-formyl-tetrahydrofolate and the folate salt is selected from calcium, sodium, zinc, arginine, choline, acetylcholine, N-methylaminoethanol, 2-amino-2-methyl-propanol, 1,1-dimethylbiquanidine, phenylethylbiquanidine, diaminoguanidine, glucosamine, and dimethylaminoethanol.

16. The method according to claim 15, wherein the eye disease is glaucoma, diabetic retinopathy, and/or age-related macular degeneration.

17. The method according claim 15, wherein the intraocular pressure is reduced below 20 mmHg.

18. The method according to claim 15, wherein the preparation is administered for at least 10 days.

19. The method according to claim 15, wherein the preparation is administered topically to an eye of the patient.

20. The method according to claim 15, wherein the preparation is administered systemically to the patient.

21. The method according to claim 15 wherein a dose of 0.2 mg to 100 mg per day of the at least one folate in reduced form is administered to the patient.

22. The preparation according to claim 7, wherein the preparation comprises at least one compound selected from the group consisting of L-selenomethionine, sodium selenite, sodium hydrogen selenite, sodium selenate, Dexpanthenol, calcium-D-pantothenate, sodium-D-pantothenate, methylcobalamin, cyanocobalamin, hydroxylcobalamin, adenosylcobalamin, pyridoxine hydrochloride, pyridoxal-5'-phosphate, sodium-riboflavin-5'-phophate, riboflavin, thiamine hydrochloride, thiamine mononitrate, D-α-tocopherol, DL-α-tocopherol, D-α-tocopherol, sodium-ascorbate, potassium-ascorbate, calcium-ascorbate, L-ascorbic acid, L-ascorbyl-6-palmitate, copper gluconate, copper citrate, copper oxide, copper lysine complex, zinc oxide, zinc gluconate, zinc lactate, zinc citrate, natural orange extract, limonene, myrcene, N-acetyl-cysteine, N-acetylcysteine amide, cysteine, lipoic acid, and methionine.

* * * * *

UNITED STATES PATENT AND TRADEMARK OFFICE
CERTIFICATE OF CORRECTION

| | | |
|---|---|---|
| PATENT NO. | : 12,048,702 B2 | Page 1 of 1 |
| APPLICATION NO. | : 17/271468 | |
| DATED | : July 30, 2024 | |
| INVENTOR(S) | : Martin Ulmann, Gerd Wiesler and Josef Flammer | |

It is certified that error appears in the above-identified patent and that said Letters Patent is hereby corrected as shown below:

In the Claims

Claim 1 Line 3-4 Column 14 delete "1-dimethylbiquanidine," and insert -- 1-dimethylbiguanidine, --.
Claim 1 Line 4 Column 14 delete "phenylethylbiquanidine," and insert -- phenylethylbiguanidine, --.
Claim 9 Line 59 Column 14 delete "mga" and insert -- mg; --.
Claim 9 Line 60 Column 14 delete "mga" and insert -- mg; --.
Claim 14 Line 1 Column 16 delete "1-dimethylbiquanidine," and insert -- 1-dimethylbiguanidine, --.
Claim 14 Line 1 Column 16 delete "phenylethylbiquanidine," and insert -- phenylethylbiguanidine, --.
Claim 14 Line 2 Column 16 delete "diaminoquanidine," and insert -- diaminoguanidine, --.
Claim 15 Line 15 Column 16 delete "1-dimethylbiquanidine," and insert -- 1-dimethylbiguanidine, --.
Claim 15 Line 15 Column 16 delete "phenylethylbiquanidine," and insert
-- phenylethylbiguanidine, --.
Claim 17 Line 21 Column 16 delete "according" and insert -- according to --.
Claim 22 Line 39 Column 16 delete "phophate," and insert -- phosphate, --.

Signed and Sealed this
Twenty-ninth Day of October, 2024

*Katherine Kelly Vidal*

Katherine Kelly Vidal
*Director of the United States Patent and Trademark Office*